United States Patent
Meyer et al.

(10) Patent No.: US 9,634,285 B2
(45) Date of Patent: Apr. 25, 2017

(54) ELECTRICAL DEVICE

(71) Applicants: KONINKLIJKE PHILIPS N.V., Eindhoven (NL); PHILIPS DEUTSCHLAND GMBH, Hamburg (DE)

(72) Inventors: Jens Meyer, Aachen (DE); Soren Hartmann, Baesweiler (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/649,757

(22) PCT Filed: Nov. 18, 2013

(86) PCT No.: PCT/IB2013/060208
§ 371 (c)(1),
(2) Date: Jun. 4, 2015

(87) PCT Pub. No.: WO2014/087282
PCT Pub. Date: Jun. 12, 2014

(65) Prior Publication Data
US 2016/0020425 A1    Jan. 21, 2016

Related U.S. Application Data

(60) Provisional application No. 61/733,538, filed on Dec. 5, 2012.

(51) Int. Cl.
*H01L 51/52* (2006.01)
*G01N 21/64* (2006.01)

(52) U.S. Cl.
CPC ....... *H01L 51/5253* (2013.01); *G01N 21/643* (2013.01); *H01L 51/5237* (2013.01); *G01N 2021/6439* (2013.01)

(58) Field of Classification Search
None
See application file for complete search history.

(56) References Cited

U.S. PATENT DOCUMENTS

| 7,767,498 B2 * | 8/2010 | Moro | H01L 51/448 438/126 |
| 2006/0121613 A1 * | 6/2006 | Havens | B32B 27/08 436/3 |

(Continued)

FOREIGN PATENT DOCUMENTS

| CN | 103325959 A | 9/2013 |
| JP | 2008280414 A | 11/2008 |
| WO | 2008082362 A1 | 7/2008 |

OTHER PUBLICATIONS

Duvenhage et al "UV Exposure and Photon Degradation of ALQ3 Powders" Physica B. 407 (2012) p. 1521-1524.

Primary Examiner — Michael Lebentritt
Assistant Examiner — Jordan Klein

(57) ABSTRACT

The invention relates to an electrical device comprising an electrical unit (2) like an organic light emitting diode, a protection element (3) like a thin film encapsulation, which at least partly covers the electrical unit, for protecting the electrical unit against water and/or oxygen, and a detection layer (4) arranged between the protection element and the electrical unit or within the protection element, wherein the detection layer comprises organic material and is adapted such that a property of the detection layer is changed, if the detection layer is in contact with a contact gas usable for detecting a permeability of the protection element. This allows easily integrating a fast detection test for detecting a permeability of the protection element into a production process for producing the electrical device, i.e. a time consuming external permeability test may not be required.

9 Claims, 4 Drawing Sheets

(56) References Cited

U.S. PATENT DOCUMENTS

| | | | | |
|---|---|---|---|---|
| 2007/0212792 A1* | 9/2007 | Havens | ............... | G01M 3/226 436/172 |
| 2008/0138538 A1* | 6/2008 | Lewis | ............... | H01L 51/5253 428/1.1 |
| 2008/0237872 A1* | 10/2008 | Nagayama | ............ | H01L 22/34 257/773 |
| 2010/0291685 A1* | 11/2010 | Zhang | ............... | G01N 21/643 436/5 |
| 2010/0294024 A1* | 11/2010 | Kumar | ................ | B82Y 30/00 73/38 |
| 2011/0127498 A1* | 6/2011 | Jung | ................ | H01L 51/5237 257/40 |
| 2012/0098421 A1* | 4/2012 | Thompson | ............ | B32B 27/08 313/512 |
| 2012/0313136 A1* | 12/2012 | Chung | .............. | H01L 51/5253 257/100 |

* cited by examiner

US 9,634,285 B2

ELECTRICAL DEVICE

CROSS-REFERENCE TO PRIOR APPLICATIONS

This application is the U.S. National Phase application under 35 U.S.C. §371 of International Application No. PCT/IB2013/060208, filed on Nov. 18, 2013, which claims the benefit of U.S. Provisional Patent Application No. 61/733,538, filed on Dec. 5, 2012. These applications are hereby incorporated by reference herein.

FIELD OF THE INVENTION

The invention relates to an electrical device comprising a protection element like a thin-film encapsulation (TFE) for protecting an electrical unit of the electrical device against water and/or oxygen, a detection apparatus for detecting a permeability of the protection element and a corresponding detection method. The invention relates further to a production apparatus and a production method for producing the electrical device.

BACKGROUND OF THE INVENTION

Organic light emitting devices are very sensitive to moisture. For this reason organic light emitting devices generally comprise a TFE, which may comprise a single inorganic layer or a combination of inorganic and/or organic layers forming a multilayer stack. The TFE generally provides a good protection against moisture. However, the quality of the TFE barrier may be reduced due to pinholes or voids, thereby providing penetration pathways for moisture through the TFE.

U.S. Pat. No. 7,767,498 B2 discloses a system for testing the effectiveness of barrier structures. The system uses metallic calcium coupons on glass encapsulated with multilayer barrier stacks. The formation of transparent calcium oxide and hydroxide by permeation increases the transmission of visible light through the calcium coupon, which can be optically detected for determining a degree of permeability of the multilayer barrier stacks. This calcium test is technically relatively complex and takes a relatively long time.

SUMMARY OF THE INVENTION

It is an object of the present invention to provide an electrical device comprising an electrical unit and a protection element for protecting the electrical unit against water and/or oxygen, a detection apparatus for detecting a permeability of the protection element of the electrical device and a corresponding detection method, which allow for a faster detection of the permeability of the protection element. The invention relates further to a production apparatus and a production method for producing the electrical device.

In a first aspect of the present invention an electrical device is presented, wherein the electrical device comprises:
an electrical unit,
a protection element, which at least partly covers the electrical unit, for protecting the electrical unit against water and/or oxygen,
a detection layer arranged between the protection element and the electrical unit or within the protection element, wherein the detection layer comprises organic material and is adapted such that a property of the detection layer is changed, if the detection layer is in contact with a contact gas usable for detecting a permeability of the protection element.

Since the detection layer comprises organic material and changes its property, if it is in contact with the contact gas usable for detecting the permeability of the protection element and since this detection layer is arranged between the protection element and the electrical unit or within the protection element, a detection test for detecting a permeability of the protection element can easily be integrated into a production process for producing the electrical device, i.e. a time consuming external permeability test as disclosed in the above mentioned patent document U.S. Pat. No. 7,767,498 B2 is not required. For instance, penetration paths for water, in particular for moisture, and/or oxygen through the protection element can be detected relatively fast during the production process by detecting the change of the property of the detection layer comprising the organic material. Particularly pinholes or other defects leading to penetration paths can be detected relatively fast.

The contact gas is preferentially a gas selected from the group consisting of water, oxygen, ozone, flourine, bromine, chlorine and combinations thereof. However, also other gases can be used, which can penetrate through defected parts of the protection element. The contact gas can be a gas having gas molecules being smaller or equal to the size of ozone molecules, further preferred smaller than or equal to the size of oxygen molecules, and even further preferred smaller than or equal to the size of water molecules.

The electrical unit is preferentially an organic light emitting unit like an organic light emitting diode (OLED), and the protection element is preferentially a TFE, which may comprise a single inorganic layer or several inorganic and/or organic layers forming a multilayer stack.

It is preferred that the detection layer is adapted such that the property of the detection layer is locally changed at a location, at which the detection layer is in contact with the contact gas. This allows determining at which location a defect like a penetration path through the protection element is present, wherein then at the determined location the defect can be repaired.

It is also preferred that the detection layer is adapted to change its property by a chemical reaction with the contact gas. The chemical reaction is preferentially a photochemical reaction. For performing the photochemical reaction light having a certain wavelength may be used like ultraviolet (UV) light. This allows modifying the property of the detection layer in a relatively simple and reliable way such that a contact of the detection layer with the contact gas can be detected with relatively high accuracy.

In a preferred embodiment the detection layer is adapted to change its property such that the change is observable by an optical measuring device. In particular, the detection layer is adapted to change at least one of the group of photoluminescence, reflectivity and absorption, if the detection layer is in contact with with the contact gas, in particular with moisture and/or oxygen.

If the change in the property should be optically detected, the protection element may be at least partly transparent with respect to light used for optically detecting the property change. If the protection element is a TFE having multiple layers and if the detection layer is arranged in between these layers of the TFE, only one or several layers of the TFE arranged between the detection layer and a light source of the measuring device may be at least partly transparent to the light emitted by the light source, in order to allow the light to traverse these one or several layers of the TFE such that it can reach the detection layer for detecting a possible property change.

The detection layer may have a thickness in the nanometer or micrometer range.

In an embodiment the detection layer may comprise a photoluminescent organic layer which is adapted such that it degrades, if the detection layer is in contact with the contact gas, in order to change its property. The photoluminescent organic layer may be photodegradable, wherein it degrades, if the photoluminescent organic layer is illuminated by light and if it is in contact with the contact gas. In particular, the photoluminescent organic layer may be adapted to degrade, if the photoluminescent organic layer is illuminated by UV light and if it is in contact with the contact gas. The photoluminescent organic layer is, for instance, Tris-(8-hydroxyquinoline)aluminum ($Alq_3$). In a further embodiment the detection layer comprises a monomer, which polymerizes, if illuminated and if in contact with the contact gas, in order to change its property. The monomer is preferentially an organic monomer like an organic photoresist. The polymerization is preferentially initiated by UV light. Using these detection layers allows detecting a contact with the contact gas with high accuracy, in particular spatially resolved.

In a further aspect of the present invention a detection apparatus for detecting a permeability of a protection element of an electrical device as defined in claim 1 is presented, wherein the protection element at least partly covers an electrical unit of the electrical device and is adapted to protect the electrical unit against water and/or oxygen, wherein the detection apparatus comprises a measuring device for measuring a change in a property of a detection layer of the electrical device, which is generated, if the detection layer is in contact with a contact gas usable for detecting the permeability of the protection element. The measuring device is preferentially adapted to optically detect the change in the property of the layer. In particular, the measuring device is adapted to use one of the group of optical microscopy, optical spectroscopy, reflective measurements, absorption measurements and luminance measurements or combinations thereof, wherein the optical microscopy may be near field scanning optical microscopy (SNOM).

In a further aspect of the present invention a production apparatus for producing an electrical device as defined in claim 1 is presented, wherein the production apparatus comprises:
an electrical unit providing unit for providing an electrical unit,
a protection element and detection layer providing unit for providing a protection element for protecting the electrical unit against water and/or oxygen and for providing a detection layer, wherein the detection layer comprises organic material and is adapted to change a property of the detection layer, if the detection layer is in contact with a contact gas usable for detecting a permeability of the protection element, wherein the protection element and the detection layer are provided such that the protection element at least partly covers the electrical unit and that the detection layer is arranged between the protection element and the electrical unit or within the protection element.

In a further aspect of the present invention a detection method for detecting a permeability of a protection element of an electrical device as defined in claim 1 is presented, wherein the protection element at least partly covers an electrical unit of the electrical device and is adapted to protect the electrical unit against water and/or oxygen, the detection method comprising measuring a change in a property of a detection layer of the electrical device, which is generated, if the detection layer is in contact with a contact gas usable for detecting the permeability of the protection element.

In another aspect of the present invention a production method for producing an electrical device as defined in claim 1 is presented, wherein the production method comprises:
providing an electrical unit,
providing a protection element for protecting the electrical unit against water and/or oxygen and a detection layer, wherein the detection layer comprises organic material and is adapted such that a property of the detection layer is changed, if the detection layer is in contact with a contact gas usable for detecting a permeability of the protection element, wherein the protection element and the detection layer are provided such that the protection element at least partly covers the electrical unit and that the detection layer is arranged between the protection element and the electrical unit or within the protection element.

The detection layer and/or the protection layer may be provided by a deposition technique like thermal evaporation, sputtering, spin coating, chemical vapor deposition, atomic layer deposition or molecular layer deposition.

It shall be understood that the electrical device of claim 1, the detection apparatus of claim 11, the production apparatus of claim 13, the detection method of claim 14, and the production method of claim 15 have similar and/or identical preferred embodiments, in particular, as defined in the dependent claims.

It shall be understood that a preferred embodiment of the invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
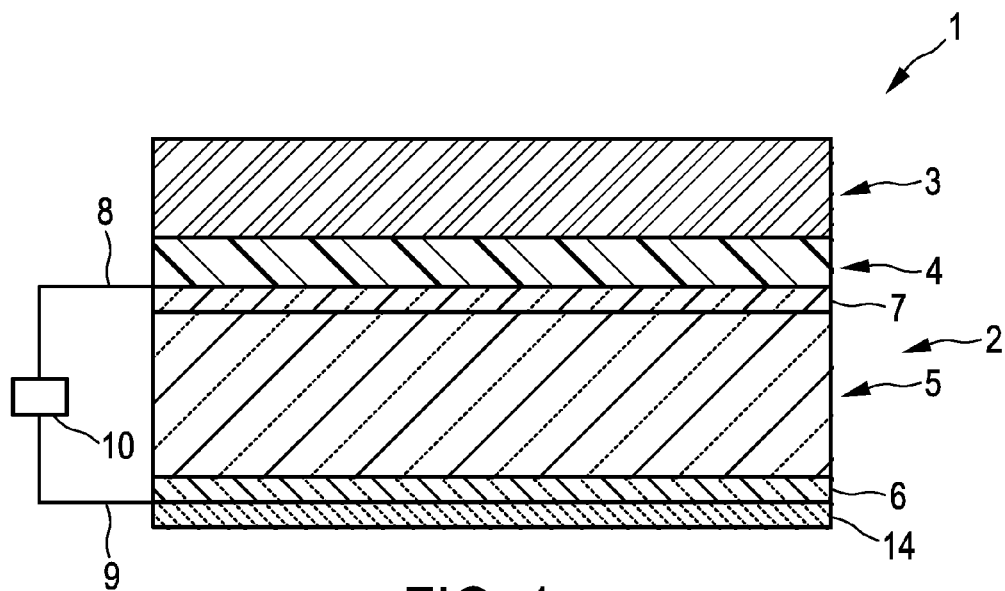
FIG. 1 shows schematically and exemplarily an embodiment of an electrical device comprising an OLED and a TFE for protecting the OLED against moisture and/or oxygen.

FIG. 1 shows schematically and exemplarily an embodiment of an electrical device. The electrical device comprises an electrical unit 2 being, in this embodiment, an OLED. The OLED comprises a transparent anode 6 on a glass substrate 14, a cathode 7 and intermediate organic light emitting layers 5. The anode 6 and the cathode 7 are electrically connected to a voltage source 10 via electrical connections 8, 9. In another embodiment the electrical unit 2 can be another kind of OLED. The electrical unit 2 can also not be an OLED, but another electrical unit that should be protected against moisture and/or oxygen.

The electrical device 1 further comprises a protection element 4, which covers the electrical unit 2, for protecting the electrical unit 2 against moisture and oxygen. In this embodiment the protection element is a TFE. Moreover, the electrical device 1 comprises a detection layer 4 arranged between the TFE 3 and the electrical unit 2, wherein the detection layer 4 is adapted such that a property of the detection layer 4 is changed, if the detection layer 4 is in contact with moisture and/or oxygen.

Figure 2:
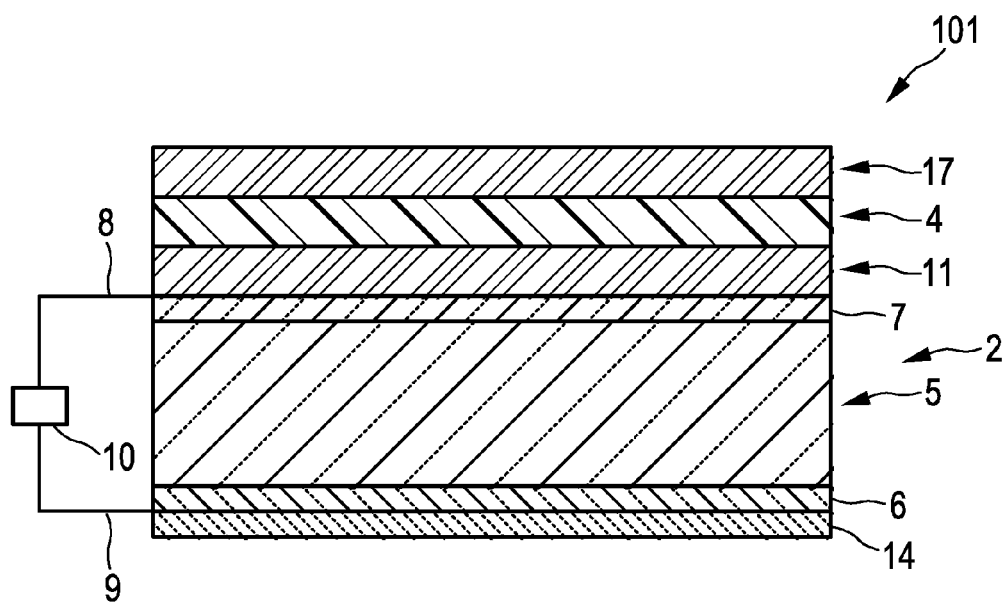
FIG. 2 shows schematically and exemplarily a further embodiment of an electrical device comprising an OLED and a TFE for protecting the OLED against moisture and/or oxygen.

The detection layer 4 can also be arranged within the TFE as schematically and exemplarily shown in FIG. 2. In FIG. 2, a further embodiment of an electrical device 101 is shown, which is similar to the electrical device 1 shown in FIG. 1, except for the TFE 11, 17 and the location of the detection layer 4. In this embodiment the TFE is a multilayer stack having at least two parts 11, 17, wherein the detection layer 4 is arranged between these two parts 11, 17 of the TFE.

The TFE comprises one or several nitride and/or oxide layers. For instance, the TFE can comprise a layer selected from the group consisting of $SiN_x$, $AlO_x$, $TiO_x$, $ZrO_x$, $HfO_x$, $SiO_x$, SiON and combinations thereof. However, the TFE can also comprise layers made of other materials. The layers of the TFE have preferentially thicknesses in the range of 10 nm to several micrometers. If the TFE layers are deposited by using an atomic layer deposition technique, a layer of the several layers of the TFE can have a thickness being smaller than 10 nm.

The detection layer 4 is adapted such that the property of the detection layer 4 is locally changed at a location, at which the detection layer 4 is in contact with moisture and/or oxygen. This property change can be provided by a chemical, in particular a photochemical reaction, with moisture, i.e. water, and/or oxygen. For performing the photochemical reaction light having a certain wavelength like UV light may be used. The property change is then preferentially observable by an optical measuring device. For instance, by the chemical reaction the photoluminescence and/or the reflectivity and/or the absorption of the detection layer can be modified at the location, at which the detection layer is in contact with moisture and/or oxygen, wherein this change in photoluminescence and/or reflectivity and/or absorption can be detected by the optical measuring device.

The detection layer 4 has a thickness in the nanometer or micrometer range and comprises an organic material and optionally additionally inorganic material. For instance, the detection layer may comprise a photoluminescent organic layer which is adapted such that it degrades, if the detection layer 4 is in contact with moisture and/or oxygen. In particular, the photoluminescent organic layer is preferentially photodegradable, wherein it degrades, if the photoluminescent organic layer is illuminated by light and if it is in contact with moisture and/or oxygen. For example, this light can be UV light and the photoluminescent organic layer can be tris-(8-hydroxyquinoline)aluminum ($Alq_3$).

The detection layer may also comprise a photoluminescent organic material which is locally degradable in an ozone or oxygen plasma process. Thus, an ozone or oxygen plasma can be applied to the electrical device, in order to degrade the photoluminescent organic material locally at locations, at which the protection element comprises penetration paths, through which moisture and oxygen may penetrate. In this case the photoluminescent organic material may be, for example, tris-(8-hydroxyquinoline)aluminum ($Alq_3$), N,N'-bis (Inaphthyl)-N,N'-diphenyl-1,1'-biphenyl-4,4'-diamine (NPB) or another one. Also another kind of plasma could be used for locally degrading the photoluminescent organic material.

In a further embodiment, the detection layer 4 may comprise a monomer, which polymerizes, if illuminated and if in contact with moisture and/or oxygen, in order to change its property. The monomer is preferentially an organic monomer like an organic photoresist, wherein the polymerization is preferentially initiated by UV light.

Figure 3:
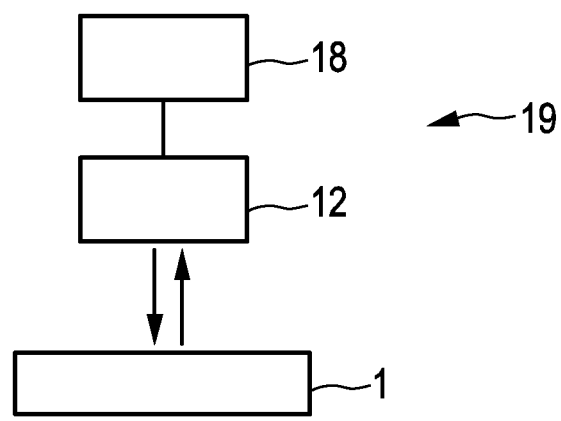
FIG. 3 shows schematically and exemplarily an embodiment of a detection apparatus for detecting a permeability of the TFE of the electrical devices shown in FIGS. 1 and 2.

FIG. 3 shows schematically and exemplarily an embodiment of a detection apparatus for detecting the permeability of the TFE of the electrical device 1, 101. The detection apparatus 19 comprises a measuring device 12 for optically measuring a change in the property of the detection layer 4 of the electrical device 1 and an output unit 18 like a display for outputting the detection result. The optical measuring device 12 can be an optical microscope, an optical spectroscope, a reflective measuring device, an absorption measuring device and/or a luminance measuring device. If the measuring device 12 is an optical microscope, it can be a near field scanning optical microscope. The measuring device 12 can comprise an UV light source for illuminating the electrical device 1 for photoactivating a desired chemical reaction, if the detection layer 4 is in contact with moisture and/or oxygen.

The detection apparatus 19 is adapted to perform a detection method for detecting the permeability of the TFE of the electrical device 1, 101, wherein the detection method comprises optically measuring the change in the property of the detection layer 4 of the electrical device.

Figure 4:
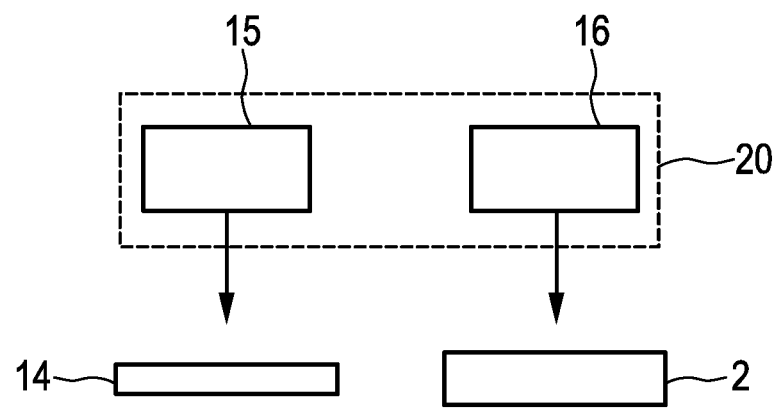
FIG. 4 shows schematically and exemplarily an embodiment of a production apparatus for producing the electrical devices shown in FIGS. 1 and 2.

FIG. 4 shows schematically and exemplarily an embodiment of a production apparatus for producing an electrical device. The production apparatus 20 comprises an electrical unit providing unit 15 for providing the electrical unit 2, in this embodiment, the OLED 2, and a protection element and detection layer providing unit 16 for providing the TFE 3 or 11, 17 and for providing the detection layer 4. In this embodiment the electrical unit providing unit 15 is adapted to deposit different layers of the OLED 2 on the substrate 14 for generating the OLED 2. Then, on the OLED 2 the protection element and detection layer providing unit 16 deposits the different layers forming the combination of the TFE and the detection layer, wherein the TFE and the detection layer are deposited such that the TFE at least partly covers the OLED 2 and that the detection layer is arranged between the TFE and the OLED or within the TFE. Thus, that the TFE covers the OLED does not mean that the TFE is necessarily in contact with the OLED, but the TFE can cover the OLED, while the detection layer is arranged in between the TFE and the OLED or while an inner part 11 of the TFE and the detection layer 4 are arranged in between an outer part 17 of the TFE and the OLED 2 as schematically and exemplarily shown in FIG. 2.

For depositing the different layers of the OLED and the TFE known deposition techniques can be used. Also for the deposition of the detection layer known deposition techniques can be used like thermal evaporation, sputtering, spin coating, chemical vapor deposition, atomic layer deposition or molecular layer deposition.

Figure 5:
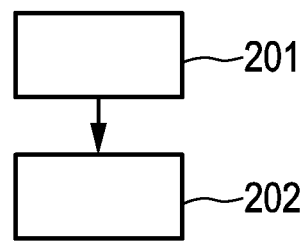
FIG. 5 shows a flowchart exemplarily illustrating an embodiment of a production method for producing the electrical devices shown in FIGS. 1 and 2.

In the following an embodiment of a production method for producing an electrical device will exemplarily be described with reference to a flowchart shown in FIG. 5.

In step 201 the electrical unit providing unit 16 provides the OLED 2. In particular, the different layers of the OLED 2 are deposited on the substrate 14 in step 201. In step 202 the protection element and detection layer providing unit 16 provides the protection element and the detection layer such that the protection element at least partly covers the electrical unit, in particular the OLED, and the detection layer is arranged between the protection element and the electrical unit or within the protection element. Preferentially, in step 202 one or several TFE layers and the detection layer are deposited by the protection element and detection layer providing unit 16 on the OLED 2, wherein the detection layer may be deposited in between the TFE and the OLED or the detection layer may be deposited between different layers of the TFE.

The defect size within a TFE may be very small such that the penetration rate of water and oxygen through the barrier may be very low. As a result, degradation effects in OLEDs due to water and oxygen may occur temporally delayed, depending on the barrier quality, after days, months or years. It is therefore beneficial to have a fast metrology to qualify the TFE directly after applying it on an OLED. This allows minimizing rejections due to imperfections and allows repairing defects in the barrier, i.e. in the protection element. Moreover, spatially resolved defect detection may allow for tracing single pinholes which can then individually be fixed.

The detection layer, which may also be regarded as being a tracing layer, preferentially acts as an optical tracer of defects in the barrier, i.e. in the protection element, due to a chemical, in particular photochemical, reaction with water and/or oxygen. The detection layer reacts with water and/or oxygen in such a way that it can be monitored with optical analysis techniques. The reaction may be provided by an organic material of the detection layer, which changes its photoluminescence and/or reflectivity and/or absorption in the presence of water and/or oxygen. The detection layer preferentially allows for a precise, non-destructive and fast detection of defects within the protection element, in particular, within the TFE barrier.

Although in above described embodiments the protection element is a TFE, in other embodiments the protection element can also be another element for protecting an electrical unit against water and/or oxygen. For instance, another layer not being a layer of a TFE can be used as protection element, as long as this layer protects the electrical unit against water and/or oxygen.

The detection apparatus for detecting a permeability of the TFE of the electrical device described above with reference to FIG. 3 can be integrated into the production apparatus for producing the electrical device described above with reference to FIG. 4 such that during the production process a degree of permeability of the TFE can be determined. This knowledge about the degree of permeability of the TFE, in particular of the location of possible penetration paths through the TFE, can be used for repairing the respective defects in the TFE. For instance, if, after one or several TFE layers have been applied on a detection layer, the permeability detection process reveals an unacceptable degree of permeability, an additional TFE layer can be deposited globally or locally at the detected defect locations, in order to fix the permeability problem. Additional TFE layers can be deposited, until the detected degree of permeability is acceptable.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Procedures like the provision of the electrical unit, of the detection layer and the protection element performed by one or several units or devices can be performed by any other number of units or devices.

Any reference signs in the claims should not be construed as limiting the scope.

The invention claimed is:

1. An electrical device comprising:
   an electrical unit;
   a protection element that at least partly covers the electrical unit for protecting the electrical unit against at least one of water or oxygen; and
   a detection layer arranged between the protection element and the electrical unit or within the protection element,
   wherein the detection layer comprises organic material and is adapted such that a property of the detection layer is changed in response to being in contact with a contact gas usable for detecting a permeability of the protection element, and
   wherein the detection layer comprises a monomer that polymerizes in response to being illuminated and to being in contact with the contact gas in order to change the property.

2. The electrical device as defined in claim 1, wherein the detection layer is adapted such that the property of the detection layer is locally changed at a location at which the detection layer is in contact with the contact gas.

3. The electrical device as defined in claim 1, wherein the detection layer is adapted to change the property by a chemical reaction with the contact gas.

4. The electrical device as defined in claim 3, wherein the chemical reaction is a photochemical reaction.

5. The electrical device as defined in claim 1, wherein the detection layer is adapted to change the property such that the change is observable by an optical measuring device.

6. The electrical device as defined in claim 1, wherein the detection layer comprises a photoluminescent organic layer which is adapted such that the photoluminescent organic layer degrades in response to the detection layer being in contact with the contact gas in order to change the property.

7. The electrical device as defined in claim 6, wherein the photoluminescent organic layer is photodegradable, wherein the photoluminescent organic layer degrades in response to the photoluminescent organic layer being illuminated and to the photoluminescent organic layer being in contact with the contact gas in order to change the property.

8. The electrical device as defined in claim 1, wherein the protection element is a thin-film encapsulation.

9. The electrical device as defined in claim 1, wherein the contact gas is at least one of water, oxygen, ozone, fluorine, bromine or chlorine.

* * * * *